US010722527B2

(12) United States Patent
Williams et al.

(10) Patent No.: US 10,722,527 B2
(45) Date of Patent: Jul. 28, 2020

(54) ABIRATERONE ACETATE LIPID FORMULATIONS

(71) Applicant: Capsugel Belgium NV, Bornem (BE)

(72) Inventors: Hywel Williams, Newport (AU); Prashant Agarwal, Waltham, MA (US); Eduardo Jule, Antwerp (BE)

(73) Assignee: Capsugel Belgium NV, Bornem (BE)

( * ) Notice: Subject to any disclaimer, the term of this patent is extended or adjusted under 35 U.S.C. 154(b) by 0 days.

(21) Appl. No.: 15/565,400

(22) PCT Filed: Mar. 25, 2016

(86) PCT No.: PCT/EP2016/056689
§ 371 (c)(1),
(2) Date: Oct. 9, 2017

(87) PCT Pub. No.: WO2016/162229
PCT Pub. Date: Oct. 13, 2016

(65) Prior Publication Data
US 2018/0125863 A1   May 10, 2018

Related U.S. Application Data

(60) Provisional application No. 62/145,864, filed on Apr. 10, 2015.

(51) Int. Cl.
*A61K 9/14* (2006.01)
*A61K 31/58* (2006.01)
*A61K 47/14* (2017.01)
*A61K 9/10* (2006.01)
*A61K 9/48* (2006.01)
*A61K 47/06* (2006.01)
*A61K 9/00* (2006.01)
*A61K 47/44* (2017.01)
*C07J 43/00* (2006.01)

(52) U.S. Cl.
CPC ............ *A61K 31/58* (2013.01); *A61K 9/0056* (2013.01); *A61K 9/10* (2013.01); *A61K 9/141* (2013.01); *A61K 9/4808* (2013.01); *A61K 47/06* (2013.01); *A61K 47/14* (2013.01); *A61K 47/44* (2013.01); *C07J 43/003* (2013.01)

(58) Field of Classification Search
None
See application file for complete search history.

(56) References Cited

U.S. PATENT DOCUMENTS

| | | | |
|---|---|---|---|
| 5,604,213 A | 2/1997 | Barrie et al. | |
| 6,572,892 B1 | 6/2003 | Ioulalen et al. | |
| 6,913,708 B2 | 7/2005 | Solomonson et al. | |
| 7,235,260 B2 | 6/2007 | Crew et al. | |
| 7,329,762 B2 | 2/2008 | Fraley et al. | |
| 7,625,507 B2 | 12/2009 | Ray et al. | |
| 7,700,766 B2 | 4/2010 | Hunt | |
| 7,741,337 B2 | 6/2010 | Van Quaquebeke et al. | |
| 7,884,107 B2 | 2/2011 | Ma et al. | |
| 7,887,844 B2 | 2/2011 | Appel et al. | |
| 7,976,871 B2 | 7/2011 | Vaya et al. | |
| 7,985,422 B2 | 7/2011 | Vaya et al. | |
| 8,158,152 B2 | 4/2012 | Palepu | |
| 8,258,140 B2 | 9/2012 | Bradbury et al. | |
| 8,476,238 B2 | 7/2013 | Ko | |
| 8,540,967 B2 | 9/2013 | Barrett et al. | |
| 8,569,348 B2 | 10/2013 | Shalwitz et al. | |
| 8,734,846 B2 | 5/2014 | Ali et al. | |
| 8,791,095 B2 | 7/2014 | Casebier et al. | |
| 8,815,879 B2 | 8/2014 | Kasina et al. | |
| 8,822,438 B2 | 9/2014 | Auerbach et al. | |
| 9,114,147 B2 | 8/2015 | Altschul et al. | |
| 9,314,473 B2 | 4/2016 | Altschul et al. | |
| 9,353,145 B2 | 5/2016 | Derrien et al. | |
| 9,511,078 B2 | 12/2016 | Desai et al. | |
| 9,522,934 B2 | 12/2016 | An et al. | |
| 9,655,868 B2 | 5/2017 | Borgstrom | |
| 9,920,089 B2 | 3/2018 | Poirier et al. | |
| 9,937,259 B2 | 4/2018 | Sun | |
| 10,010,520 B2 | 7/2018 | Cheng et al. | |
| 10,087,212 B2 | 10/2018 | Xing et al. | |
| 2003/0219490 A1 | 11/2003 | Hovey et al. | |
| 2004/0092583 A1 | 5/2004 | Shanahan-Prendergast | |
| 2006/0247221 A1 | 11/2006 | Coelingh Bennink et al. | |
| 2007/0093462 A1 | 4/2007 | Rogers et al. | |
| 2007/0298099 A1* | 12/2007 | Peresypkin .......... A61K 9/4858 424/456 |
| 2008/0004286 A1 | 1/2008 | Wang et al. | |
| 2008/0051375 A1 | 2/2008 | Auerbach et al. | |
| 2008/0051380 A1 | 2/2008 | Auerbach et al. | |
| 2009/0124587 A1 | 5/2009 | Auerbach et al. | |
| 2010/0004156 A1 | 1/2010 | Kaushal et al. | |

(Continued)

FOREIGN PATENT DOCUMENTS

EP           1336602        8/2003
IN      1013/MUM/2005      6/2007

(Continued)

OTHER PUBLICATIONS

International Search Report and Written Opinion for International Application No. PCT/EP2016/056689, dated May 12, 2016.
"Assessment Report for Zytiga (abiraterone)", Jul. 21, 2011, 78 pages.
Bhaskar et al., "Preparation and characterization of etoricoxib solid dispersions using lipid carriers by spray drying technique," AAPS Pharm SciTech, (Oct. 19, 2005), 6(3):E405-E412.
Extended European Search Report for Application No. 14832376.9, dated Jan. 30, 2017, 8 pp.
Final Office Action for U.S. Appl. No. 14/906,507, dated Nov. 27, 2017.
International Search Report and Written Opinion for PCT/AU2014/050168 (dated Oct. 10, 2014).

(Continued)

*Primary Examiner* — Susan T Tran
(74) *Attorney, Agent, or Firm* — Klarquist Sparkman, LLP

(57) ABSTRACT

Abiraterone acetate lipid formulations.

15 Claims, 1 Drawing Sheet

(56) References Cited

U.S. PATENT DOCUMENTS

| | | |
|---|---|---|
| 2010/0016409 A1 | 1/2010 | Yingling et al. |
| 2010/0029704 A1 | 2/2010 | Hanma et al. |
| 2010/0087474 A1 | 4/2010 | Kaushal et al. |
| 2010/0226943 A1 | 9/2010 | Brennan et al. |
| 2010/0233112 A1 | 9/2010 | Hu et al. |
| 2011/0033461 A1 | 2/2011 | Ratushny et al. |
| 2011/0104052 A1 | 5/2011 | Barnett et al. |
| 2011/0201563 A1 | 8/2011 | Spiegel et al. |
| 2011/0224141 A1 | 9/2011 | Thompson et al. |
| 2012/0077845 A1 | 3/2012 | Dalton et al. |
| 2012/0121692 A1 | 5/2012 | Xu et al. |
| 2012/0156138 A1 | 6/2012 | Smith |
| 2012/0295878 A1 | 11/2012 | Ferlini et al. |
| 2013/0045204 A1 | 2/2013 | Andersen et al. |
| 2013/0177625 A1 | 7/2013 | Kim et al. |
| 2013/0203714 A1 | 8/2013 | Bradbury et al. |
| 2013/0211249 A1 | 8/2013 | Barnett et al. |
| 2013/0219528 A1 | 8/2013 | Borgstrom |
| 2013/0251804 A1 | 9/2013 | Bandyopadhyay et al. |
| 2013/0280244 A1 | 10/2013 | Sidera et al. |
| 2013/0280264 A1 | 10/2013 | Davila |
| 2013/0287767 A1 | 10/2013 | Gokaraju et al. |
| 2013/0336962 A1 | 12/2013 | Andersen et al. |
| 2014/0023615 A1 | 1/2014 | Hsu et al. |
| 2014/0072529 A1 | 3/2014 | Peters et al. |
| 2014/0079636 A1 | 3/2014 | Chimmanamada et al. |
| 2014/0107085 A1 | 4/2014 | Penning et al. |
| 2014/0107180 A1 | 4/2014 | MacLeod et al. |
| 2014/0127316 A1 | 5/2014 | Omene et al. |
| 2014/0155363 A1 | 6/2014 | Marom et al. |
| 2014/0155458 A1 | 6/2014 | Almog et al. |
| 2014/0171503 A1 | 6/2014 | Neckers et al. |
| 2014/0199236 A1 | 7/2014 | Chen et al. |
| 2014/0221386 A1 | 8/2014 | Nannini et al. |
| 2014/0248211 A1 | 9/2014 | Bender et al. |
| 2014/0248263 A1 | 9/2014 | Andersen et al. |
| 2014/0255413 A1 | 9/2014 | Adam et al. |
| 2014/0287039 A1* | 9/2014 | Bosch .................. C07J 43/003 424/465 |
| 2014/0315866 A1 | 10/2014 | Pan et al. |
| 2015/0133416 A1* | 5/2015 | Grenier ................. A61K 9/145 514/176 |
| 2015/0246060 A1 | 9/2015 | Murphy et al. |
| 2016/0067265 A1 | 3/2016 | Bosch et al. |
| 2016/0151503 A1 | 6/2016 | Porter et al. |
| 2017/0119674 A1 | 5/2017 | Hojgaard |
| 2017/0315127 A1 | 11/2017 | Gao et al. |
| 2018/0243313 A1 | 8/2018 | Shuttleworth et al. |
| 2018/0271849 A1 | 9/2018 | Ge et al. |
| 2018/0318263 A1 | 11/2018 | Schlaepfer |

FOREIGN PATENT DOCUMENTS

| | | |
|---|---|---|
| JP | 2009-511497 | 3/2009 |
| TW | 201249847 | 12/2012 |
| WO | WO 93/20097 | 10/1993 |
| WO | WO 99/21534 A1 | 5/1999 |
| WO | WO 2005/053655 | 6/2005 |
| WO | WO 2006/070117 | 7/2006 |
| WO | WO 2007/044693 | 4/2007 |
| WO | WO 2008/024484 | 2/2008 |
| WO | WO 2008/062466 | 5/2008 |
| WO | WO 2008/093686 | 8/2008 |
| WO | WO 2008/127290 | 10/2008 |
| WO | WO 2008/154382 | 12/2008 |
| WO | WO 2010/111397 | 9/2010 |
| WO | WO 2010/143199 | 12/2010 |
| WO | WO 2011/032100 | 3/2011 |
| WO | WO 2011/57064 | 5/2011 |
| WO | WO 2012/013331 | 2/2012 |
| WO | WO 2012/074842 | 6/2012 |
| WO | WO 2012/077135 | 6/2012 |
| WO | WO 2012/116277 | 8/2012 |
| WO | WO 2012/135759 | 10/2012 |
| WO | WO 2012/145328 | 10/2012 |
| WO | WO 2012/145330 | 10/2012 |
| WO | WO 2012/158884 | 11/2012 |
| WO | WO 2013/012959 | 1/2013 |
| WO | WO 2013/050280 | 4/2013 |
| WO | WO 2013/67131 | 5/2013 |
| WO | WO 2013/71177 | 5/2013 |
| WO | WO 2013/79964 | 6/2013 |
| WO | WO 2013/096907 | 6/2013 |
| WO | WO 2013/126581 | 8/2013 |
| WO | WO 2013/148337 | 10/2013 |
| WO | WO 2013/152342 | 10/2013 |
| WO | WO 2013/159225 | 10/2013 |
| WO | WO 2013/164473 | 11/2013 |
| WO | WO 2013/166110 | 11/2013 |
| WO | WO 2013/184621 | 12/2013 |
| WO | WO 2014/005089 | 1/2014 |
| WO | WO 2014/009434 | 1/2014 |
| WO | WO 2014/009437 | 1/2014 |
| WO | WO 2014/047199 | 3/2014 |
| WO | WO 2014/053650 | 4/2014 |
| WO | WO 2014/058785 | 4/2014 |
| WO | WO 2014/060347 | 4/2014 |
| WO | WO 2014/060358 | 4/2014 |
| WO | WO 2014/071984 | 5/2014 |
| WO | WO 2014/095833 | 6/2014 |
| WO | WO 2014/104784 | 7/2014 |
| WO | WO 2015/000451 | 1/2015 |
| WO | WO 2015/032873 | 3/2015 |
| WO | WO 2015/114314 | 8/2015 |
| WO | WO 2016/001208 | 1/2016 |
| WO | WO 2016/044701 | 3/2016 |
| WO | WO 2016/128891 | 8/2016 |
| WO | WO 2017/037647 | 3/2017 |
| WO | WO 2017/123542 | 7/2017 |

OTHER PUBLICATIONS

International Preliminary Report on Patentability for PCT/AU2014/050168 (dated Feb. 11, 2016).

Nanjwade et al., "Functions of Lipids for Enhancement of Oral Bioavailability of Poorly Water-Soluble Drugs," Sci Pharm, 79(4):705-727 (Oct.-Dec. 2011).

Notice of Reasons for Refusal, dated Feb. 6, 2018, issued in related Application No. JP 2016-530278 (with English translation).

Office Action for European Patent Application No. 14832376.9 (dated Jul. 3, 2018).

Office Action for European Patent Application No. 16711831.4, dated Jul. 23, 2019.

Office Action for U.S. Appl. No. 14/906,507, dated May 2, 2017.

Office Action for U.S. Appl. No. 14/906,507, dated Mar. 4, 2019.

Preeti et al., "Formulation and In-vitro Characterization of Self-Nanoemulsifying Drug Delivery System of Cinnarizine," International Journal of Comprehensive Pharmacy; Sep. 2011, 9(08) pp. 1-6.

Restriction Requirement for U.S. Appl. No. 14/906,507, dated Nov. 25, 2016.

Saq-Fachgruppe Pharma et al., "Oral Formulations for Poorly Water Soluble Compounds", Jun. 23, 2009, XP055325894, Retrieved from the Internet: URL: http://www.pharma.gally.ch/UserFiles/File/Kalb%20schwerloesliche%20Wirkstoffe.pdf [retrieved on Dec. 5, 2016], 41 pp.

Stoimenovski, J., et al., "Crystalline vs. Ionic Liquid Salt Forms of Active Pharmaceutical Ingredients: A Position Paper," Pharmaceutical Research, vol. 27, No. 4, pp. 521-526 (Apr. 2010).

International Search Report issued for International Application No. PCT/EP2016/056689 dated Apr. 29, 2016.

\* cited by examiner

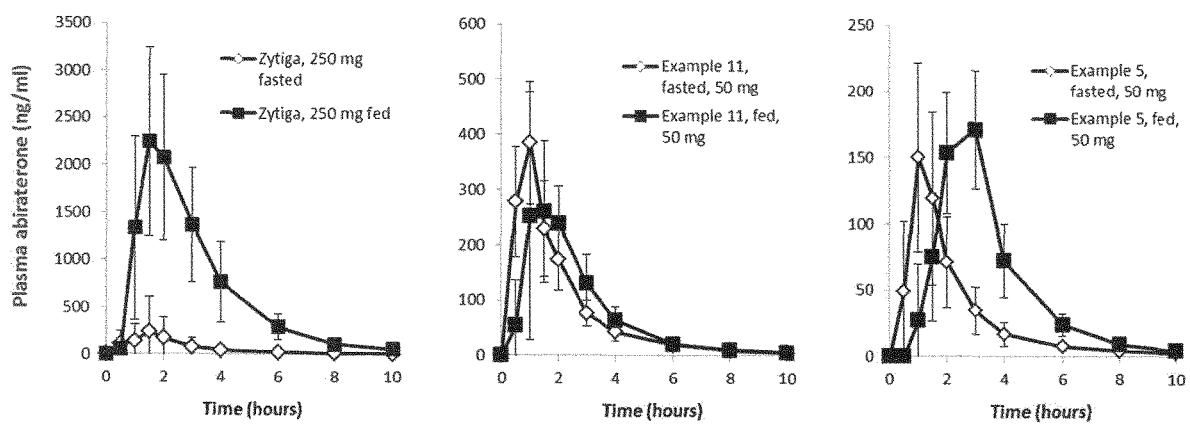

ABIRATERONE ACETATE LIPID FORMULATIONS

CROSS REFERENCE TO RELATED APPLICATIONS

This is the U.S. National Stage of International Application No. PCT/EP2016/056689, filed Mar. 25, 2016, which was published in English under PCT Article 21(2), which in turn claims the benefit of U.S. Provisional Application No. 62/145,864, filed Apr. 10, 2015.

FIELD

Disclosed are lipid compositions comprising abiraterone acetate.

BACKGROUND

Lipid multiparticulates (LMPs) are known. See for example EP1030687, U.S. Pat. No. 6,572,892, EP1827382, U.S. Pat. Nos. 7,235,260, 7,887,844, EP1691787, U.S. Pat. No. 7,625,507.

Abiraterone acetate (Zytiga® tablets) was developed by Janssen, and approved in 2011 for use in combination with prednisone for the treatment of patients with metastatic castration-resistant prostate cancer. Abiraterone acetate has the following structure:

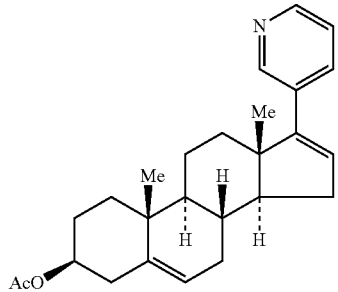

Abiraterone acetate is a prodrug of abiraterone, which inhibits 17 α-hydroxylase/C17,20-lyase (CYP17) expressed in testicular, adrenal, and prostatic tumor tissues. Abiraterone acetate is highly lipophilic (Log P 5.12) and as a result suffers from low aqueous solubility in the gastrointestinal tract. Zytiga® tablets containing abiraterone acetate show a clinically significant positive food effect when administered with low-fat (7- and 5-fold increase in $C_{max}$ and $AUC_{0-\infty}$, respectively) or high-fat (17- and 10-fold increase in $C_{max}$ and $AUC_{0-\infty}$, respectively). As a result, patients taking Zytiga® need to avoid food for at least 2 hours before administration and at least one hour after. There is a benefit in developing a new abiraterone acetate formulation that improves bioavailability in the fasted state to in turn reduce the food effect and overall variability in absorption.

SUMMARY

Disclosed are compositions comprising abiraterone acetate and a lipid matrix. In one embodiment the lipid matrix comprises a) at least one fatty acid ester, b) at least one surfactant, and c) optionally an antioxidant. In one embodiment the abiraterone acetate comprises at least 0.2 wt % of the composition, at least one fatty acid ester comprises at least 10 wt % of the composition, at least one surfactant comprises at least 10 wt % of the composition. In one embodiment, the compositions are liquid at ambient temperature. In one embodiment, the compositions are semi-solid at ambient temperature. In one embodiment, abiraterone is molecularly dispersed in the lipid matrix.

In one embodiment, the lipid matrix comprises a) at least one low flow point excipient, b) at least one high flow point excipient, c) at least one low-flow point surfactant, and c) optionally an antioxidant. In one embodiment, the abiraterone acetate comprises at least 0.2 wt % of the composition, the at least one low flow point excipient comprises at least 10 wt % of the composition, the at least one high flow point excipient comprises at least 5 wt % of the composition, and the at least one low-flow point surfactant comprises at least 10 wt % of the composition. In one embodiment, the compositions comprise a plurality of particles that are solid at ambient temperature, have a generally spherical shape, and have a mean diameter ranging from 40 μm to 3000 μm.

In another embodiment, the lipid matrix is a liquid or semi-solid at ambient temperature.

In another embodiment, the compositions of the invention are filled into capsules.

In one embodiment, the compositions are administered orally to a patient in need of therapy.

In one embodiment, the lipid matrix is selected from the group consisting of fatty alcohols, fatty acids, fatty acid esters of glycerol, glycols and poly glycols, fatty acid esters of polyglycerol, polyglycolized glycerides, C8-C18 triglycerides, stearoyl polyoxylglycerides, lauroyl macrogol-32 glycerides, caprylocaproyl macrogol-8 glycerides, oleoyl macrogol-6 glycerides, linoleoyl macrogol-6 glycerides, myristyl alcohol, lauryl alcohol, capric alcohol, glycerol behenate, glycerol dibehenate, glycerol palmitate, hydrogenated castor oil, stearyl alcohol, behenyl alcohol, palmitic acid, stearic acid, paraffin wax, beeswax, candelilla wax, carnauba wax, polyethoxylated 12-hydroxysteric acid, propylene glycol monocaprylate esters, propylene glycol dicaprate/dicaprylate esters, propylene glycol heptanoate, propylene glycol monostearate, propoylene glycol monooleate, propylene glycol monopalmitate, propylene glycol monomyristate, esterified alpha-tocopheryl polyethylene glycol succinate, propylene glycol monolaurate esters, polyoxyl 35 castor oil, polyoxyl 40 hydrogenated castor oil, lecithins, vitamin E, tocopheryl polyethylene glycol succinate (TPGS), sugar fatty acid esters, sorbitan fatty acid esters, polyoxyethylene sorbitan fatty acid esters, polyoxyethylene-polyoxypropylene copolymers, propylene glycol, triacetin, isorpropyl myristate, diethylene glycol monoethyl ether, polyethylene glycol, glycerol, rosemary extract, ascorbic acid, ascorbyl palmitate, butylated hydroxyanisole (BHA), butylated hydroxytoluene (BHT), and mixtures and combinations thereof.

BRIEF DESCRIPTION OF THE DRAWINGS

FIG. 1 shows graphs of measured abiraterone (ng/ml) in plasma due to complete conversion from abiraterone acetate as a function of time (hours).

DETAILED DESCRIPTION

The present disclosure relates to lipid compositions for abiraterone acetate, such as lipid multiparticulate formulations comprising abiraterone acetate and a lipid matrix or liquid fill hard capsules comprising abiraterone acetate and a lipid matrix.

The following description is exemplary in nature and is not intended to limit the scope, applicability, or configuration of the invention in any way. Various changes to the described embodiments may be made in the function and arrangement of the elements described herein without departing from the scope of the invention.

As used in this application and in the claims, the singular forms "a," "an," and "the" include the plural forms unless the context clearly dictates otherwise. Additionally, the term "includes" means "comprises." Further, the term "coupled" generally means electrically, electromagnetically, and/or physically (e.g., mechanically or chemically) coupled or linked and does not exclude the presence of intermediate elements between the coupled or associated items absent specific contrary language.

Unless otherwise indicated, all numbers expressing quantities of ingredients, properties such as molecular weight, percentages, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Definitions

As used in the present disclosure, the following words, phrases, and symbols are generally intended to have the meanings as set forth below, except to the extent that the context in which they are used indicates otherwise.

As used herein, "optional" or "optionally" means that the subsequently described material, event or circumstance may or may not be present or occur, and that the description includes instances where the material, event or circumstance is present or occurs and instances in which it does not.

As used herein, "w/w %" and "wt %" means by weight as a percentage of the total weight or relative to another component in the composition.

The term "about" is intended to mean approximately, in the region of, roughly, or around. When the term "about" is used in conjunction with a numerical range, it modifies that range by extending the boundaries above and below the numerical values set forth. Unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques.

The term excipient is meant any pharmaceutically acceptable ingredient that is included in the formulation that is not the active agent. The term glyceride is meant a fatty acid ester of glycerol. By "fatty acid ester of glycerol" is meant mono, di, and tri esters of glycerides. Glycerides also include glycerol esters that have both fatty acid and poly alkyl oxide esters.

As used herein, the term "flow point" is the temperature at which any portion of the mixture becomes sufficiently fluid that the mixture, as a whole, may be atomized. Generally, a mixture is sufficiently fluid for atomization when the viscosity of the molten mixture is less than 20,000 cp, or less than 15,000 cp, or less than 10,000 cp, less than 5000 cp, or even less than 1000 cp. The viscosity can be measured by controlled stress rheometer, which measures viscosity as a function of temperature, and may use either a shear-type or rotational rheometer. As used herein, melting point refers to the temperature that marks the midpoint of the transition from a solid crystalline or semi-crystalline state to a liquid state. As measured by DSC, the melting point is the temperature where upon heating the solid material, the maximum exothermic heat flow occurs. In general, melting point will be used in reference to relative pure single component materials such as some actives or essentially single component excipients (e.g. stearyl alcohol) and flow point will be used in reference to multi-component materials or mixtures.

The term "ambient temperature" refers to a temperature of 20° C.

As used herein, the term "semi-solid" is a solid at ambient temperature, but becomes a liquid at temperatures above 30° C. or 40° C., or at body temperature.

Unless otherwise indicated, "capsule" means a container suitable for enclosing solids or liquids, and includes empty capsule shells and components thereof such as caps and bodies that may be assembled together to form the capsule.

Unless otherwise indicated, "dosage form" refers to a solid composition comprising an active ingredient.

Active Agents

Embodiments of the disclosed compositions include abiraterone acetate, or a pharmaceutically acceptable salt form. The compositions may contain one or more active agents. As used herein, by "active" or "active agent" is meant a drug, medicament, pharmaceutical, therapeutic agent, nutraceutical, or other compound that may be desired to be administered to the body.

In some embodiments, the active agent is crystalline in the compositions. In other embodiments, the active agent is non-crystalline in the compositions. In still another embodiment, the active agent may comprise crystalline and non-crystalline regions in the compositions. In some embodiments, the active agent is at least 60 wt % crystalline. In other embodiments, the active agent is at least 75 wt % crystalline. In another embodiment, the active agent is at least 90 wt % crystalline. In other embodiments, the active may dissolve into the excipients prior to forming the compositions. During the multiparticulate formation process, a portion of the crystalline active agent may dissolve into the excipient mixture up to the active agent's solubility limit in the excipient mixture at the processing conditions. When the excipient mixture is cooled to form the multiparticulates, the multiparticulate will comprise particles of crystalline active agent encapsulated in a solid solution of excipient and the dissolved active agent.

Lipid Excipients

The lipid multiparticulates include fatty alcohols, fatty acids, fatty acid esters of glycols and poly glycols, fatty acid esters of polyglycerol and fatty acid esters of glycerol (glycerides) with flow points of less than 50° C. When the low flow point excipient is a relatively pure material, the melting point is also less than 50° C. A preferred class of low flow point excipients are low flow point glycerides. By "low flow point" excipient, such as a glyceride, is meant that the melting point of the excipient, such as a glyceride, is less than 50° C. In some embodiments, the low flow point glyceride has a melting point of less than 40° C. In some embodiments, the low-flow point excipients are liquids at ambient temperature (typically at temperatures of from about 20° C. to about 25° C., preferably about 25° C.). Exemplary low flow point excipients include glycerol monooleate (such as Peceol™ predominantly mono and dioleate ($C_{18}$ esters of glycerol), $C_8$ to $C_{10}$ triglycerides (Miglyol 812®, caprylic, $C_8$, and capric acid, $C_{10}$ triglycerides), and glycerol monocaprylate (Imwitor 308®, mono and dicaprylate, $C_8$ esters of glycerol; also some monodicaprate acid, $C_{10}$ glycerol esters).

In some embodiments, the low-flow point excipient, such as glyceride, is a mixture of compounds, having a flow point of 50° C. or less. In some embodiments, the low-flow point excipient, such as glyceride, has a flow point of 40° C. or less. In some embodiments, the low-flow point glyceride has a low flow point of 30° C. or less.

Exemplary low-flow point glycerides include polyglycolized glycerides, such as some of the Gelucire products manufactured by Gattefosse, such as Gelucire® 43/01 having a nominal melting point of 43° C. Mixtures of low flow point glycerides are also effective, such as mixtures of Gelucire® 43/01 ($C_{10}$-$C_{18}$ triglycerides), Gelucire® 50/13 (stearoyl polyoxylglycerides), Gelucire® 44/14 (lauroyl macrogol-32 glycerides), Gelucire® 48/16 (polyoxyl stearate), and mixtures thereof. Other glycerides may also be used, such as fatty acid esters of glycols and poly glycols, and fatty acid esters of polyglycerols.

A function of the low flow point excipient is to ensure that at least a significant portion of the formulation matrix softens when ingested orally by a patient in need of therapy, at the temperature of the GI tract (about 37° C. for humans). This allows the formulation to break down by digestion in the gastro-intestinal (GI) tract, and ultimately to disperse in the GI tract to promote dissolution and absorption of the active. In certain embodiments the low flow point excipient provides a significant portion of the formulation matrix to be present in a non-crystalline liquid or amorphous state when ingested and softened in the GI tract.

Exemplary low flow point fatty alcohols include myristyl alcohol (Tm 38° C.), lauryl alcohol (Tm 23° C.) and capric alcohol (Tm 7° C.).

High Flow Point Excipients

Exemplary high flow point glycerides include glycerol behenate, glycerol dibehenate, glycerol palmitate, hydrogenated castor oil, and mixtures thereof. Often, the high flow point glyceride is a mixture of compounds that are formulated into a product and sold under a variety of trade names.

Exemplary high flow point and high melt point fatty alcohols include stearyl alcohol (Tm 58° C.) and behenyl alcohol (Tm 71° C.).

Exemplary high flow point and high melt point fatty acids include palmitic acid (Tm 63° C.) and stearic acid (Tm>70° C.).

Exemplary waxes include paraffin wax, beeswax, candelilla wax, carnauba wax, and mixtures thereof.

A function of the high flow point excipient is to aid in the manufacturability of the LMPs by enabling the LMP to congeal at a lower temperature to obtain solid particles during a melt-spray-congeal process. In certain embodiments the high flow point excipient aids the physical stability of the LMP formulation. In most embodiments, the high flow point excipient is not appreciably digested in the GI tract.

Other Excipients Including Surfactants, Co-Surfactants, and Antioxidants

In some embodiments, the LMPs include other excipients to improve the performance and chemical stability of the formulations. In some embodiments, surfactants and co-surfactants may be included in the compositions. Exemplary surfactants and co-surfactants include polyethoxylated 12-hydroxysteric acid, also known as PEG15 hydroxystearate (Kolliphor® HS-15), propylene glycol monocaprylate ($C_8$) esters (Caproyl™ 90), esterified alpha-tocopheryl polyethylene glycol succinate (TPGS), mono, di, tricaprylic ($C_8$) and capric acid ($C_{10}$) esters of glycerol and mono and diesters of PEG400 (Labrasol®), Propylene glycol monolaurate ($C_{12}$) esters (Labrafil® M1944CS), Polyoxyl 40 hydrogenated castor oil (Kolliphor® RH40), lecithins, and mixtures thereof.

In one embodiment, the LMPs optionally include an antioxidant to maintain chemical stability of the abiraterone acetate. Exemplary antioxidants include vitamin E, tocopheryl polyethylene glycol succinate (TPGS), rosemary extract, ascorbic acid, ascorbyl palmitate, butylated hydroxyanisole (BHA), butylated hydroxytoluene (BHT), and mixtures and combinations thereof.

In some embodiments, a flow aid is used to improve the flow properties of the LMPs. Exemplary flow aids also known as glidants include calcium silicate, cab-o-sil, silicon dioxide, calcium phosphate tribasic, colloidal silicone dioxide, magnesium silicate, magnesium trisilicate, starch, talc, and other flow aids.

Lipid Excipients

In one embodiment, the lipid excipient is selected from the group comprising fatty alcohols, fatty acids, fatty acid esters of glycols and poly glycols, fatty acid esters of glycerol, polyglycerol, polyglycolized glycerides, $C_{10}$-$C_{18}$ triglyceridesstearoyl polyoxylglycerides, lauroyl macrogol-32 glycerides, caprylocaproyl macrogol-8 glycerides, oleoyl macrogol-6 glycerides, linoleoyl macrogol-6 glycerides, myristyl alcohol, lauryl alcohol, capric alcohol, glycerol behenate, glycerol dibehenate, glycerol palmitate, hydrogenated castor oil, stearyl alcohol, behenyl alcohol, palmitic acid, stearic acid, paraffin wax, beeswax, candelilla wax, carnauba wax, polyethoxylated 12-hydroxysteric acid, propylene glycol fatty acid esters, esterified alpha-tocopheryl polyethylene glycol succinate, mono, propylene glycol monolaurate ($C_{12}$) esters, polyoxyl 35 castor oil, polyoxyl 40 hydrogenated castor oil, lecithins, vitamin E, tocopheryl polyethylene glycol succinate (TPGS), sugar fatty acid esters, sorbitan fatty acid esters, polyoxyethylene sorbitan fatty acid esters, polyoxyethylene-polyoxypropylene copolymers, rosemary extract, ascorbic acid, ascorbyl palmitate, butylated hydroxyanisole (BHA), butylated hydroxytoluene (BHT), propylene glycol, triacetin, isorpropyl myristate, diethylene glycol monoethyl ether, polyethylene glycol, glycerol, and mixtures and combinations thereof. Such lipid excipients may be suitable for liquid fill hard capsule compositions.

Examples of $C_{10}$-$C_{18}$ triglyderides include but are not limited to glycerol tricaprylate, glycerol tricaprate, glycerol trilaurate, glyceryl triolein, glyceryl tristearate, glyceryl tripalmitate, almond oil, canola oil, cod liver oil, corn oil, cottonseed oil, evening primrose oil, fish oil, grape seed oil, olive oil, palm kernel oil, palm oil, peanut oil, rapeseed oil, safflower oil, sesame oil, soybean oil, sunflower oil, hydrogenated coconut oil, hydrogenated cottonseed oil, hydrogenated palm oil, hydrogenated soybean oil, partially hydrogenated soybean oil and hydrogenated vegetable oil.

Examples of fatty acid esters of glycerol include but are not limited to glycerol monolinoleate, glycerol monooleate, glycerol monostearate, glycerol monocaprylate and glycerol monocaprate, which are sold under various trade names such as Peceol™, Maisine 35-1, Geleol®, Capmul® and Imwitor.

Examples of propylene glycol fatty acid esters include but are not limited to propylene glycol monocaprylate, dicaprate/dicaprylate esters, propylene glycol heptanoate, propylene glycol monolaurate, propylene glycol monostearate, propoylene glycol monooleate, propylene glycol monopalmitate, propylene glycol monomyristate, which are sold under various trade names such as Capryol®, Lauroglycol®, Labrafac® and Capmul®.

Examples of sorbitan fatty acid esters include but are not limited to sorbitan monolaurate, sorbitan monopalmitate, sorbitan monooleate and sorbitan trioleate, which are sold under various trade names such as Span® and Montane®.

Examples of polyoxyethylene sorbitan fatty acid esters include but are not limited to polysorbate 20, polysorbate 40, polysorbate 60, polysorbate 80 and polysorbate 85, which are sold under various trade names such as Tween® and Montanox®.

Examples of the polyoxylglycerides are already listed, for example, oleoyl macrogol-6 glycerides, linoleoyl macrogol-6 glycerides, and lauroyl macrogol-6 glycerides These are sold under different trade names such as Labrasol®, Gelucire® and Labrafil®. Preferred embodiments of the composition for liquid (and/or solid/semi-solid) fill hard capsules (and/or soft capsules) are described in the table below:

| Component | Excipient | Range wt % of composition |
|---|---|---|
| Fatty acid esters of glycerol | Glycerol monooleate (e.g., Peceol); glycerol monolinoleate (eg Maisine 35-1) or glycerol monostearate (eg Geleol) or mixtures of triglyceride with these monoglycerides, for example 1:0.5, 1:1, 1:2, 1:3 or 1:4 triglyceride/monoglyceride ratios These long-chain triglycerides could be corn oil, soybean oil, peanut oil etc | 10-60% wt |
| Propylene glycol fatty acid esters or polyoxylglycerides | Propylene glycol monocaprylate (Capryol ™ 90); propylene glycol dicaprate/dicaprylate esters, propylene glycol heptanoate, propylene glycol monolaurate, propylene glycol monostearate, propoylene glycol monooleate, propylene glycol monopalmitate, propylene glycol monomyristate (Capryol ®, Lauroglycol ®, Labrafac ® and Capmul), also oleoyl macrogol-6 glycerides (Labrafil ® M1944CS), linoleoyl macrogol-6 glycerides (Labrafil ® M2125CS) and lauroyl macrogol-6 glycerides (Labrafil ® M2130CS) | 20-60% wt |
| Surfactant | Polyoxyl 40 hydrogenated castor oil (Kolliphor ® RH40): polysorbates (polysorbate 20, polysorbate 40, polysorbate 60, polysorbate 80 and polysorbate 85), polyoxyl 35 castor oil (Kolliphor EL), polyethoxylated 12-hydroxysteric acid (Solutol HS-15), vitamin E, tocopheryl polyethylene glycol succinate (TPGS), caprylocaproyl macrogol-8 glycerides (Labrasol), lauroyl macrogol-32 glycerides (Gelucire 44/14) and macrogol stearate (Gelucire 48/16), or mixtures of these surfactants | 15-60% wt |

In one embodiment the lipid matrix comprises:
(a) a fatty acid ester of glycerol or mixtures thereof in an amount of from 10 to 60 wt % of said composition;
(b) at least one of a propylene glycol fatty acid ester and/or a polyoxylglyceride in an amount of from 20 to 60 wt % of said composition;
(c) a surfactant present in an amount of from 15 to 60 wt %.

In one embodiment the fatty acid ester of glyercol is selected from the group consisting of glycerol tricaprylate, glycerol tricaprate, glycerol trilaurate, glyceryl triolein, glyceryl tristearate, glyceryl tripalmitate, almond oil, canola oil, cod liver oil, corn oil, cottonseed oil, evening primrose oil, fish oil, grape seed oil, olive oil, palm kernel oil, palm oil, peanut oil, rapeseed oil, safflower oil, sesame oil, soybean oil, sunflower oil, hydrogenated coconut oil, hydrogenated cottonseed oil, hydrogenated palm oil, hydrogenated soybean oil, partially hydrogenated soybean oil and hydrogenated vegetable oil, glycerol monolinoleate, glycerol monooleate, glycerol monostearate, glycerol monocaprylate and glycerol monocaprate.

In one embodiment the lipid propylene glycol fatty acid ester is selected from the group consisting of propylene glycol monocaprylate, propylene glycol dicaprate/dicaprylate esters, propylene glycol heptanoate, propylene glycol monolaurate, propylene glycol monostearate, propoylene glycol monooleate, propylene glycol monopalmitate, and propylene glycol monomyristate; and the polyoxylglyceride is selected from the group consisting of oleoyl macrogol-6 glycerides, linoleoyl macrogol-6 glycerides and lauroyl macrogol-6 glycerides.

In one embodiment the surfactant is selected from the group consisting of Polyoxyl 40 hydrogenated castor oil, polysorbates, polyoxyl 35 castor oil, polyethoxylated 12-hydroxysteric acid, vitamin E, tocopheryl polyethylene glycol succinate (TPGS), caprylocaproyl macrogol-8 glycerides, lauroyl macrogol-32 glycerides, and macrogol stearate, or mixtures of these surfactants.

In one embodiment the composition the lipid matrix comprises
(a) a fatty acid ester of glycerol present in an amount of from 20 to 40 wt % of the composition;
(b) at least one of a propylene glycol fatty acid ester and a polyoxylglyceride present in an amount of from 20 to 40 wt % of the composition; and
(c) the surfactant is present in an amount of from 20 to 40 wt %.

In one embodiment the fatty acid ester of glycerol is selected from the group consisting of glycerol monolinoleate, glycerol monooleate, glycerol monostearate, glycerol monocaprylate and glycerol monocaprate.

In one embodiment the propylene glycol fatty acid ester is selected from the group consisting of propylene glycol monocaprylate, propylene glycol dicaprate/dicaprylate esters, propylene glycol heptanoate, propylene glycol monolaurate, propylene glycol monostearate, propoylene glycol monooleate, propylene glycol monopalmitate, and propylene glycol monomyristate.

In one embodiment the fatty acid ester of glycerol is glycerol monooleate and the propylene glycol fatty acid ester is propylene glycol monocaprylate.

Physical Properties of the Lipid Matrix

In one embodiment, the compositions of the present invention are liquid at ambient temperature. Such formulations can be filled into hard capsules, or softgel capsules. In another embodiment, the compositions of the invention are semi-solids, and may be filled into hard capsules or softgel capsules.

In another embodiment, compositions comprise a plurality of particles that are solid at ambient temperature and are generally spherical in shape, having a size ranging from a mean diameter of 40 µm to 3000 µm, or even 50 µm to 1000 µm, or even 100 µm to 300 µm. In some embodiments, the LMPs comprising abiraterone acetate and all excipients that make up the matrix have a flow point above 25° C. In some embodiments, the flow point is above 30° C. or 35° C. or 40° C. In some embodiments, the flow point of the LMP composition is less than 50° C. or less than 40° C. By generally spherical is meant that while most particles are essentially spherical, they do not necessarily form "perfect" spheres. Such particle variations in spherical shapes are known to those persons of ordinary skill in the art of melt-spray-congeal processing and similar particulate forming methods. To measure the diameters of the particulates, there are several methods that can be used, including laser diffraction, optical microscopy, and/or SEM.

Lipid formulations are advantageous active agent forms because they are amenable for use in scaling dosage forms according to the weight of an individual animal, including humans, in need of treatment by simply scaling the mass of particles in the dosage form to comport with the animal's weight. They are further advantageous since they allow the incorporation of a large quantity of active into a simple dosage form such as a capsule. Lipid formulations also have numerous therapeutic advantages over other dosage forms, especially when taken orally, including (1) improved dispersal in the gastrointestinal (GI) tract, (2) relatively rapid and reproducible passage from the stomach, (3) more uniform GI tract transit time, and (4) reduced inter- and intra-patient variability.

Compositions

In some embodiments, the compositions comprise abiraterone acetate, at least one fatty acid ester, at least one surfactant, and optionally an antioxidant. In one embodiment, the abiraterone acetate comprises at least 0.2 wt % of the composition, the fatty acid ester comprises at least 10 wt % of the composition, the surfactant comprises at least 10 wt % of the composition. In still another embodiment, the abiraterone acetate comprises at least 3 wt % of the composition, the fatty acid ester comprises at least 25 wt % of the composition, the surfactant comprises at least 40 wt % of the composition. In yet another embodiment, the abiraterone acetate comprises at least 5 wt % of the composition, the fatty acid ester comprises at least 40 wt % of the composition, and surfactant comprises at least 30 wt % of the composition. In one embodiment, the abiraterone acetate comprises at least 10 wt % of the composition, the fatty acid ester comprises at least 30 wt % of the composition, the surfactant comprises at least 50 wt % of the composition. In some embodiments, a low dose of the active may lead to improved bioavailability when dosed orally to a patient in need of therapy.

In some embodiments, the abiraterone acetate comprises at least 2 wt % of the compositions, at least 3 wt % of the compositions, at least 5 wt % of the compositions, at least 7 wt % of the compositions, or at least 10 wt % of the compositions.

In another embodiment, the compositions comprise abiraterone acetate, at least one low-flow point excipient, at least one high flow point excipients, at least one low-flow point surfactant, and optionally an antioxidant. In one embodiment, the abiraterone acetate comprises at least 0.2 wt % of the composition, the low flow-point excipient comprises at least 10 wt % of the composition, the high flow-point excipient comprises at least 5 wt % of the composition, and the low-flow point surfactant comprises at least 10 wt % of the composition. In still another embodiment, the abiraterone acetate comprises at least 5 wt % of the composition, the low flow-point excipient comprises at least 20 wt % of the composition, the high flow-point excipient comprises at least 5 wt % of the composition, and the low-flow point surfactant comprises at least 30 wt % of the composition.

In some embodiments, the abiraterone acetate comprises at least 2 wt % of the compositions, at least 3 wt % of the compositions, at least 5 wt % of the compositions, at least 7 wt % of the compositions, or at least 10 wt % of the compositions.

The LMP formulations also comprise a low flow point excipient. In one embodiment, the LMP matrix is comprised of at least 10 wt % to 50 wt % of the low flow point excipient. In another embodiment, the LMP formulation is comprised of at least 50 wt % to 75 wt % of the low flow point excipient.

The LMP formulations also comprise a high flow point excipient. In one embodiment, the compositions comprise at least 2 wt % of the high flow point excipient. In another embodiment, the LMP matrix is comprised of 1 wt % to 30 wt % of the high flow point excipient. In still another embodiment, the LMP matrix is comprised of 2 wt % to 20 wt % of the high flow point excipient. In still another embodiment, the LMP matrix is comprised of 3 wt % to 15 wt % of the high flow point excipient.

The LMP formulations may also comprise an antioxidant. In one embodiment, the LMP formulations comprise from 0 wt % to 20 wt %, such as from 0.01 wt % to 20 wt %, of an antioxidant. In one embodiment, the LMP formulations comprise from 1 wt % to 15 wt % of an antioxidant.

The LMP formulations may also comprise a flow aid. In one embodiment, the LMP formulations may comprise from 0 wt % to 5 wt %, such as from 0.01 wt % to 5 wt %, of a flow aid. In another embodiment, the LMP formulations may comprise from 0.5 wt % to 2 wt % of a flow aid.

In some embodiments, the compositions comprise an active agent, a low flow point excipient, and a high flow point excipient, where in the mass ratio of active agent is from 0.2 wt % to 60 wt %, the mass ratio of low flow point excipient from 10 wt % to 50 wt %, and the high flow point excipient ranges from 1 wt % to 30 wt % of the composition. In other embodiments, the mass ratio of active agent is from 5 wt % to 20 wt % of the composition, the mass ratio of the low flow point excipient is 50 wt % to 75 wt % of the composition, and the mass ratio of the high flow point excipient ranges from 2 wt % to 20 wt % of the composition. In still another embodiment, the mass ratio of active agent is from 5 wt % to 15 wt % of the composition, the mass ratio of the low flow point excipient is 50 wt % to 75 wt % of the composition, and the mass ratio of the high flow point excipient ranges from 3 wt % to 15 wt % of the composition.

In one embodiment, the compositions comprise from 5 wt % to 10 wt % of the active agent, from 60 wt % to 80 wt % of the low flow point excipient, from 2 wt % to 12 wt % of an antioxidant, from 2 wt % to 20 wt % of a high flow point excipient, and from 1 wt % to 10 wt % of a dispersing agent.

In some embodiments, the compositions comprise from 5 wt % to 10 wt % of the active agent, from 60 wt % to 80 wt % of the low flow point excipient, from 2 wt % to 12 wt % of an antioxidant, from 2 wt % to 20 wt % of a high flow point excipient, and from 1 wt % to 10 wt % of a dispersing agent.

In other embodiments, the compositions comprise from 5 wt % to 10 wt % of the active agent, from 60 wt % to 80 wt % of the low flow point excipient, from 2 wt % to 12 wt % of an antioxidant, from 2 wt % to 20 wt % of a high flow point excipient, and from 1 wt % to 10 wt % of a flow aid.

In a preferred embodiment, the compositions herein comprise, preferably consist of, from 3 wt % to 10 wt %, preferably from 4 wt % to 7 wt % of abiraterone acetate; from 10 wt % to 60 wt %, preferably from 20 wt % to 50 wt %, more preferably from 25 wt % to 35 wt %, more preferably from 27 wt % to 29 wt %, of a fatty acid ester of glycerol (preferably glycerol monooleate, like commercially available Peceol™) or mixtures thereof; from 20 wt % to 60 wt %, preferably from 30 wt % to 50 wt %, more preferably from 32 wt % to 33 wt %, of at least one of a propylene glycol fatty acid ester (preferably Propylene glycol monocaprylate, like commercially available Capryol™ 90) or a polyoxylglyceride (like commercially available Gelucire™, Labrasol™, Labrafil™); and from 20 wt % to 60 wt %, preferably from 30 wt % to 50 wt %, more preferably from 32 wt % to 33 wt %, of a surfactant typically selected from a hydrogenated castor oil (preferably Polyoxyl 40 hydrogenated castor oil, like commercially available Kolliphor® RH40). The compositions herein may be in the form of an isotropic clear solution.

Processes for Making the Compositions

In one embodiment, the following process is used to prepare the compositions. The active-free formulation is prepared by weighing the appropriate excipients into a vessel, and melting if necessary. The excipients are then mixed thoroughly to generate an isotropic solution. The mass of the abiraterone acetate is then added, and the active-free formulation is mixed at 50° C. until the active is completely dissolved (usually confirmed by polarized light microscopy). The final formulation is then cooled to ambient temperature for storage until filled into a capsule.

In another embodiment, the compositions may be formed by a "melt-spray-congeal" process, as described below. See, for example, U.S. Pat. Nos. 7,235,260, 7,887,844, EP1691787, U.S. Pat. No. 7,625,507.

A molten mixture is formed by mixing and heating the compositions. Such compositions are comprised of abiraterone acetate, and a lipid matrix. "Molten mixture" means that the mixture of abiraterone acetate and lipid matrix materials are sufficiently mixed and heated to fluidize the mixture sufficiently to allow it to be atomized into droplets. Generally, the mixture is molten in the sense that it will flow when subjected to one or more forces such as pressure, shear, and centrifugal force, such as that exerted by a centrifugal or spinning-disk atomizer.

Once the molten mixture has been formed, it is delivered to an atomizer that breaks the molten mixture into small droplets. Virtually any method can be used to deliver the molten mixture to the atomizer. In certain embodiments of the disclosed methods the molten mixture is delivered to the atomizer by use of pumps and/or various types of pneumatic devices such as pressurized vessels or piston pots or extruder. In certain embodiments the molten mixture is maintained at an elevated temperature during delivery to the atomizer to prevent its solidification and to keep it in a flowable state.

When a centrifugal atomizer (also known as rotary atomizers or spinning-disk atomizer) is used, the molten mixture is fed onto a rotating surface, where it spreads outward and flows by centrifugal force. The rotating surface may take several forms, examples of which include a flat disk, a cup, a vanned disk, and a slotted disk. The surface of the disk may also be heated to aid in atomization of the molten mixture or cooled to aid in the solidification of the LMPs. Several mechanisms of atomization are observed with flat-disk and cup centrifugal atomizers, depending on the flow of molten mixture to the disk, the rotation speed of the disk, the diameter of the disk, the viscosity of the feed, and the surface tension and density of the feed. At low flow rates, the molten mixture spreads out across the surface of the disk and when it reaches the edge of the disk, forms a discrete droplet, which is then flung from the disk.

Once the molten mixture has been atomized, the droplets are congealed, typically by contact with a gas at a temperature below the solidification temperature of the composition. Typically, it is desirable that the droplets are congealed in less than 60 seconds, less than 10 seconds, or even in less than 1 second. In certain embodiments congealing at ambient temperature using an ambient temperature cooling medium, results in sufficiently rapid solidification of the droplets. However, as certain embodiments of the disclosed compositions are comprised of at least 50 wt % of a low flow point excipient, it is often advantageous to utilize a cooling medium that is at a temperature that is at least 10° C. below ambient temperature. For some embodiments, it is preferred to utilize a cooling medium that is at least 20° C. below ambient temperature.

Dosage Forms

In one embodiment, the compositions of the invention are placed into a capsule for delivery by oral ingestion. Exemplary capsules include hard gelatin capsules, soft gelatin capsules, HPMC capsules as well as capsules made from other materials. The compositions may also be filled as a liquid into the capsule. The LMPs can also be suspended in a liquid such as an aqueous solution and then ingested. The LMPs may also be sprinkled on food and then ingested. The LMPs may also be mixed with solid excipients and then compressed into tablets.

Liquid-filled capsules can be hard or soft in form and may conveniently deliver the active within a liquid formulation. The fill formulation can contain either solubilized or suspended active, dependent on the choice of formulation, active solubility in this formulation and the dose per capsule. There is a performance advantage to the development of liquid formulations in which the active is pre-solubilized within the fill formulation since this active does not require further dissolution in the GI tract. This is important since the dissolution of the active in the GI tract can be rate-limiting to the absorption of poorly water-soluble drugs. Other advantages of liquid-filled capsules over other dosage forms such as tablets and caplets include better patient compliance, greater flexibility in dosage form design, and less expensive manufacturing process.

Liquid-filled two piece hard capsules (LFHC) may be produced from a range of materials, with gelatin and hydrophilic polymers often the preferred choice. In addition to these polymers, the capsule shell may also contain a pharmaceutically acceptable plasticizer, coloring agents and lubricants. Hard capsule shells are generally manufactured using dip molding processes.

LFHC may be used for a number of different applications including bioavailability enhancement of poorly water-soluble molecules, high-potency molecules, molecules susceptible to oxidation, molecules exhibiting low melting points, and molecules requiring controlled/sustained release formulations. The fill formulation can contain or mixtures of lipidic excipients such as those outlined above. Dependent on the composition, the fill formulation may be liquid at ambient temperature or solid/semi-solid.

Evaluation of Compositions

The compositions of the invention may be tested in vivo in animals, or in vitro using appropriate test solutions. Bioavailability of the compositions can be tested in vivo in animals or humans using conventional methods for making such a determination. An in vivo test, such as a crossover study, may be used to determine whether a composition provides an enhanced active agent concentration in the blood (serum or plasma) versus time area under the curve (AUC) for a test subject, dosed with the composition relative to the active agent concentration in the blood versus time AUC for a test subject dosed with a control composition. The bioavailability is measured as the area under the curve (AUC) determined for each group. In vivo determinations of AUC can be made by plotting the serum or plasma concentration of active agent along the ordinate (y-axis) against time along the abscissa (x-axis). Generally, the values for AUC represent a number of values taken from all of the subjects in a patient test population and are, therefore, mean values averaged over the entire test population. By measuring the AUC for a population to which the test composition has been administered and comparing it with the AUC for the same population to which the control composition has been administered, the test composition can be evaluated. The determination of AUCs is a well-known procedure and is described, for example, in Welling, "Pharmacokinetics Processes and Mathematics," ACS Monograph 185 (1986).

In one embodiment, the AUC of the test composition divided by the amount dosed is at least 1.25-fold the AUC of the control composition divided by the amount dosed. In another embodiment, the AUC of the test composition divided by the amount dosed is at least 2-fold the AUC of the control composition divided by the amount dosed. In still another embodiment, the AUC of the test composition divided by the amount dosed is at least 2.5-fold the AUC of the control composition divided by the amount dosed. In still another embodiment, the AUC of the test composition divided by the amount dosed is at least 3-fold the AUC of the control composition divided by the amount dosed.

In one embodiment, the compositions may be tested in vitro using an appropriate test solution. Exemplary test solutions include aqueous solutions at 37° C. comprising 0.1N HCl, simulating gastric fluid without enzymes, or intestinal buffer solutions, or water. Other in vitro tests solutions may be used as know by those skilled in the art.

EXAMPLES

Example 1

The following components were formulated:

| Function | Component | Amount (wt %) |
|---|---|---|
| Active | Abiraterone acetate | 10.0 |
| Lipid phase | Glycerol monooleate (Peceol ™) | 31.5 |
| Cosurfactant | Propylene glycol monolaurate (Lauroglycol ™ 90) | 31.5 |
| Surfactant | PEG15 hydroxystearate (Kolliphor ® HS-15) | 27.0 |

The active-free formulation was prepared first by weighing the appropriate amount of each of the above excipients into a glass vial, with prior excipient melting, if needed. Excipients were then mixed thoroughly to generate an isotropic solution. The target mass of active (abiraterone acetate) was then added to another glass vial followed by the active-free formulation and mixing at 50° C. until the active was completely dissolved (confirmed by polarized light microscopy). The final formulation was a pale yellow liquid, with evidence of some excipient solids on prolonged storage at room temperature.

On in vitro dispersion in 250 mL degassed water (37° C.), 1 g of Example 1 formed a homogenous cloudy dispersion, with no evidence of active crystals over a 6 h time-period.

Example 1, containing an additional 0.1% butylated hydroxytoluene (BHT) antioxidant, was placed on accelerated stability for 1 month. The active recrystallized at 25° C./60% RH while samples stored at 40° C./75% RH were physically stable (no crystals) and chemically stable (0.3% total impurities).

Example 2

The following components were formulated:

| Function | Component | Amount (wt %) |
|---|---|---|
| Active | Abiraterone acetate | 10.00 |
| Lipid phase | Glycerol monocaprylate (Imwitor 308 ®) | 33.75 |
| Cosurfactant | Propylene glycol monocaprylate (Capryol ™ 90) | 33.75 |
| Surfactant | TPGS (Kolliphor ® TPGS) | 22.50 |

The active-free formulation was prepared first by weighing the appropriate amount of each of the above excipients into a glass vial, with prior excipient melting, if needed. Excipients were then mixed thoroughly to generate an isotropic solution. The target mass of active (abiraterone acetate) was then added to another glass vial followed by the active-free formulation and mixing at 30° C. until the active was completely dissolved (confirmed by polarized light microscopy). The final formulation was a clear colorless liquid.

On in vitro dispersion in 250 mL degassed water (37° C.), 1 g of Example 2 formed a homogenous cloudy dispersion, with no evidence of active crystals over a 6 h time-period.

Example 2, containing an additional 0.1% BHT antioxidant, was placed on accelerated stability for 1 month. No physical or chemically (0.0% total impurities) instabilities were seen.

Example 3

The following components were formulated:

| Function | Component | Amount (wt %) |
|---|---|---|
| Active | Abiraterone acetate | 10.0 |
| Lipid phase | Propylene glycol monocaprylate (Capryol ™ 90) | 54.0 |
| Cosurfactant | PEG-8 caprylic/capric acid glycerides (Labrasol ®) | 18.0 |
| Surfactant | PEG15 hydroxystearate (Kolliphor ® HS-15) | 18.0 |

The active-free formulation was prepared first by weighing the appropriate amount of each of the above excipients into a glass vial, with prior excipient melting, if needed. Excipients were then mixed thoroughly to generate an isotropic solution. The target mass of active (abiraterone acetate) was then added to another glass vial followed by the active-free formulation and mixing at 30° C. until the active was completely dissolved (confirmed by polarized light microscopy). The final formulation was a clear, colorless liquid.

On in vitro dispersion in 250 mL degassed water (37° C.), 1 g of Example 3 formed a homogenous milky dispersion, with no evidence of active crystals over a 6 h time-period.

Example 3, containing an additional 0.1% BHT antioxidant, was placed on accelerated stability for 1 month. No physical or chemically (0.1% total impurities) instabilities were seen.

Example 4

The following components were formulated:

| Function | Component | Amount (wt %) |
|---|---|---|
| Active | Abiraterone acetate | 10.0 |
| Lipid phase | $C_8$-$C_{10}$ triglycerides (Miglyol 812 ®) | 13.5 |
| Cosurfactant | Propylene glycol monocaprylate (Capryol ™ 90) | 54.0 |
| Surfactant | PEG15 hydroxystearate (Kolliphor ® HS-15) | 22.5 |

The active-free formulation was prepared first by weighing the appropriate amount of each of the above excipients into a glass vial, with prior excipient melting, if needed. Excipients were then mixed thoroughly to generate an isotropic solution. The target mass of active (abiraterone acetate) was then added to another glass vial followed by the active-free formulation and mixing at 30° C. until the active was completely dissolved (confirmed by polarized light microscopy). The final formulation was a clear colorless liquid.

On in vitro dispersion in 250 mL degassed water (37° C.), 1 g of Example 4 formed a homogenous cloudy to transparent dispersion, with no evidence of active crystals over a 6 h time-period.

Example 4, containing an additional 0.1% BHT antioxidant, was placed on accelerated stability for 1 month. No physical or chemically (0.1% total impurities) instabilities were seen.

In Vitro Digestion Tests to Identify Best Performing Abiraterone Acetate Formulation at 10.0% wt Loading: Example 1, 2, 3 and 4

In vitro digestion tests were performed as follows: 1 g of each active-containing formulation was dispersed in 40 mL fasted intestinal medium (2 mM Tris-maleate, 1.4 mM $CaCl_2 \cdot 2H_2O$, and 150 mM NaCl, 3 mM sodium taurodeoxycholate and 0.75 mM phosphatidylcholine, 37° C.) using a pH-stat titrator as described by the LFCS Consortium (Williams, H D. et al., J. Pharm. Sci. 101 (2012), p. 3360-3380). Digestion was initiated on addition of 4 mL porcine pancreatic extract, prepared as described previously (Williams, H D. et al., J. Pharm. Sci. 101 (2012), p. 3360-3380), and continuously monitored and maintained at pH 6.5 with 0.2 or 0.6 M NaOH for 60 min during which period samples were removed, centrifuged to produce a multiphase sample consisting of; a pellet phase, containing any precipitated active; an aqueous phase, containing the active in free solution and active solubilized in small micelles and vesicles; and sometimes a lipid phase, containing the active solubilized in undigested oil droplets and/or larger colloids such as multi-lamellar vesicles. Active concentrations in these phases were measured by HPLC. The performance of Examples 1, 2, 3 and 4 on digestion are summarized below:

| Digestion time point | Solubilized (lipid + aq. phase) active concentration (μg/mL) | | | |
|---|---|---|---|---|
|  | Example 1 | Example 2 | Example 3 | Example 4 |
| −5 min | 2411 | 3018 | 2755 | 2937 |
| 0 min | 2392 | 3094 | 2805 | 2841 |
| 5 min | 1555 | 2195 | 2551 | 2647 |
| 15 min | 1642 | 1756 | 2360 | 2547 |
| 30 min | 1416 | 1478 | 2374 | 2593 |
| 45 min | 1000 | 1329 | 2200 | 2573 |
| 60 min | 657 | 1421 | 2250 | 2515 |
| Colloidal distribution of the active @ 60 min: | | | | |
| Lipid phase | 9% | — | 68% | 84% |
| Aq. phase | 30% | 57% | 22% | 17% |
| Pellet phase | 59% | 34% | 5% | 2% |

The results show that all lipid formulations example were able to solubilize the active at concentrations much higher than the equilibrium solubility of the crystalline active in the same medium (without the digested lipid formulation), which was measured at 27 μg/mL. Example 1 and 2 showed evidence of active precipitation on digestion, as evidenced by the progressive decrease in solubilized concentrations with respect to time and the analysis of the pellet phase at 60 min. Example 3 and 4 were more robust, showing negligible active precipitation on digestion. In both cases, the majority of the active was solubilized in a lipid phase that phase-separated on centrifugation of the samples and most likely consisting of larger lipophilic colloids including multi-lamellar vesicles. Active drug in the aqueous phase (consisting of BS/PL mixed-micelles, lipid-enriched BS/PL mixed micelles and small vesicles) is considered the most readily available form for absorption.

Examples 6-9 at Lower 7% w/w Active Loading

The following components were formulated:

| Component | Amount (wt %) | | | |
|---|---|---|---|---|
|  | Example 6 | Example 7 | Example 8 | Example 9 |
| Abiraterone acetate | 7.00 | 7.00 | 7.00 | 7.00 |
| Glycerol monooleate (Peceol ™) | 27.90 | 27.90 | 27.90 | 46.50 |
| Propylene glycol monolaurate (Lauroglycol ™ 90) | 32.55 | — | — | — |
| Propylene glycol monocaprylate (Capryol ™ 90) | — | 32.55 | — | — |
| PEG-6 oleyl glycerides (Labrafil ® M1944CS) | — | — | 32.55 | 23.25 |
| PEG15 hydroxystearate (Kolliphor ® HS-15) | 32.55 | — | 32.55 | 23.25 |
| Polyoxyl 40 hydrogenated castor oil (Kolliphor ® RH40) | — | 32.55 | — | — |

Active-free formulations were prepared as described for Example 1. The above examples formed isotropic solutions at 50° C. that were colorless to yellow in color depending on the composition. At lower temperatures, there was some evidence of excipient solidification, e.g., in the case of Examples 8 and 9.

Example 7 and 9 containing an additional 0.1% BHT antioxidant, were placed on accelerated stability for 1 month. The results are summarized in the table below:

|  | 25° C./60% RH | | 40° C./75% RH | |
|---|---|---|---|---|
| Impurities (%) | Physical Stability | Chemical Stability | Physical Stability | Chemical Stability |
| Example 7 - 1 month | Stable | 0.1% | Stable | 0.1% |
| Example 9 - 1 month | Stable | <0.1% | Stable | 0.32% |

Under accelerated conditions, Example 9 exhibited greater levels of unknown impurities relative to Example 7. Both Examples were physically stable over 1 month.

Example formulations 6-9 were then subjected to in vitro dispersion tests wherein 1 g of formulation was dispersed in 250 mL degassed water at 37° C. over 6 hours. The following results were obtained:

| Dispersion observations | Example 6 | Example 7 | Example 8 | Example 9 |
|---|---|---|---|---|
| Macroscopic appearance | Milky | Translucent/ Cloudy | Cloudy | Cloudy |
| Microscopic appearance | Aggregates and poorly dispersed oil droplets | No particles were evident | Poorly dispersed oil droplets | Poorly dispersed oil droplets |
| Evidence of active precipitation | No precipitation over 6 h | No precipitation over 6 h | No precipitation over 6 h | No precipitation over 6 h |

All examples provided the desirable property of precipitation of the active over 6 hours. Since the solubilization of poorly water-soluble actives is critical to absorption, Examples 6-9 may support the intestinal absorption of the active, abiraterone acetate. Example 7 exhibited superior dispersion properties and was progressed into in vitro digestion tests. These tests were performed as described above for Examples 1-4. The following results were obtained:

| Digestion time point | Solubilized (lipid + aq. phase) active concentration (μg/mL) Example 7 |
|---|---|
| −5 min | 1858 |
| 0 min | 1855 |
| 5 min | 1961 |
| 15 min | 1611 |
| 30 min | 1592 |
| 45 min | 1544 |
| 60 min | 1504 |
| Colloidal distribution of the active @ 60 min: | |
| Lipid phase | 7% |
| Aq. phase | 80% |
| Pellet phase | 13% |

Example 7 was robust to digestion, with minimal precipitation of the active to the pellet phase. Due to the optimized dispersion properties, Example 7 also provided a high percentage of active solubilized in the aqueous phase—this phase consists of small dispersed colloids including micelles and small vesicles. Solubilized active concentrations in both the aqueous phase (in which the majority (80%) of active was present) and lipid phase were >1500 μg/mL during the entire digestion test. As a comparison, the crystalline solubility of the active in the same medium was measured at 27 μg/mL.

Variations of Example 7 containing different loadings of the active were prepared in the same manner as described for Example 1:

|  | Amount (wt %) | | |
|---|---|---|---|
| Component | Example 10 | Example 11 | Example 12 |
| Abiraterone acetate | 3.00 | 6.00 | 10.00 |
| Glycerol monooleate (Peceol ™) | 29.10 | 28.20 | 27.00 |
| Propylene glycol monocaprylate (Capryol ™ 90) | 33.95 | 32.90 | 31.50 |
| Polyoxyl 40 hydrogenated castor oil (Kolliphor ® RH40) | 33.95 | 32.90 | 31.50 |

Examples 10-12 formed isotropic clear solutions that were pale yellow in color. Example 11 was placed on stability over 3 months. The following results were obtained:

|  | 5° C. | | 25° C./60% RH | | 40° C./75% RH | |
|---|---|---|---|---|---|---|
| Example 11 | Physical Stability | Chemical Stability | Physical Stability | Chemical Stability | Physical Stability | Chemical Stability |
| 1 month | Stable | <0.1% | Stable | <0.1% | Stable | <0.1% |

Examples 10-12 were tested by in vitro digestion following the same method as previously described. The following results were obtained:

| Digestion time point | Solubilized (lipid + aq. phase) active concentration (μg/mL) | | |
|---|---|---|---|
|  | Example 10 | Example 11 | Example 12 |
| −5 min | 884 | 1592 | 2505 |
| 0 min | 846 | 1691 | 2477 |
| 5 min | 719 | 1613 | 2038 |
| 15 min | 712 | 1244 | 1984 |
| 30 min | 720 | 1197 | 1972 |
| 45 min | 712 | 1226 | 1962 |
| 60 min | 646 | 1164 | 1925 |
| Colloidal distribution of the active @ 60 min: | | | |
| Lipid phase | 12% | 10% | 18% |
| Aq. phase | 75% | 80% | 76% |
| Pellet phase | 13% | 10% | 6% |

Since 1 gram of formulation was evaluated, Examples 10, 11 and 12 provided 30 mg, 60 mg and 100 mg of active, respectively, in the digestion test. The results indicate no significant change in performance with increasing active loading in the formulation as evidenced by negligible change in % active recovered in the pellet phase and high solubilized active concentrations in the aqueous and lipid phase. Indeed, comparing Examples 7, 10, 11 and 12 which utilize the same excipients in the same ratios and only differ in active loading, a linear correlation ($R^2$=0.9835) can be obtained between solubilized active concentrations following 60 min digestion and active loading in the formulation. This capacity of a formulation to maintain the active in solution across a range of active loadings is desirable for consistent in vivo performance at different doses. In addition, since good performance is maintained at a 10% w/w active loading, there is the gained knowledge that lower active loadings are not near a performance threshold. Solubilized active concentrations at the lowest loading (i.e., Example 10) were still significantly in excess of the crystalline solubility (27 μg/mL).

In Vivo Performance Assessment of Example 10 in Beagle Dogs Vs. Zytiga® Tablets The in vivo absorption of the active was assessed in a cross-over study using fasted beagle dogs (n=6). In this study, the commercial abiraterone acetate tablet (Zytiga® 250 mg) and Example 10 were both dosed. The target dose delivered by Example 10 was 25 mg, i.e., $1/10^{th}$ of the Zytiga® dose, which was achieved using approximately 0.83 mL formulation filled in hard capsules (Limps®, size 00el) prior to administration. The following results were obtained (note that results are expressed as measured plasma abiraterone due to complete conversion from abiraterone acetate in vivo):

| Treatment | Dose (mg) | $AUC_{0-24\,h}$ (h · ng/mL) ± SD | CV | $T_{max}$ (h) | Relative BA |
|---|---|---|---|---|---|
| Zytiga ® tablet fasted | 250 | 413 ± 378 | 94% | 2.4 ± 2.1 | 100.0% |
| Example 10 fasted | 25 | 227 ± 39 | 22% | 0.8 ± 0.3 | 50.6% |

The mean total absorption of the active from the commercial tablet was 413 h·ng/mL. Example 10 provided approximately 50% of this exposure (227 h·ng/mL) despite dosing the dogs only $1/10^{th}$ of the Zytiga® dose. This result therefore highlights the low absorption of the active from the fasted state using Zytiga® which contains crystalline drug and the fact that a higher proportion of the administered dose can be absorbed using lipid formulations that are effective in maintaining substantially higher solubilized abiraterone acetate concentrations (such as Example 10). In addition to supporting the total extent of absorption (captured here by AUC values), Example 10 provided a marked reduction in inter-dog absorption variability (captured here by CV, the coefficient of variation) and variability in absorption rate (captured here by the $T_{max}$) in comparison to Zytiga®. The results of this study indicate that equivalent exposure to Zytiga® may be obtained at a substantially lower dose than 250 mg. Further analyses of the above results indicate that this equivalence might be achieved at a 50 mg active dose, which may be delivered in a capsule by Example 11 with no change in total formulation volume when compared to Example 10.

In Vitro Robustness Digestion Testing of Example 11

To further test formulation robustness as a digestion condition, Example 11 was assessed on in vitro digestion under more dilute experimental conditions:

| Digestion time point | Solubilized (lipid + aq. phase) active concentration (μg/mL) | |
|---|---|---|
| | 0.33 g of Example 11 tested in 40 mL digestion medium | 0.83 g of Example 11 tested in 40 mL digestion medium |
| −5 min | 553 | 1409 |
| 0 min | 559 | 1363 |
| 5 min | 448 | 1127 |
| 15 min | 423 | 1128 |
| 30 min | 382 | 1102 |
| 45 min | 379 | 1111 |
| 60 min | 352 | 1078 |
| Colloidal distribution of the active @ 60 min: | | |
| Lipid phase | 6% | 4% |
| Aq. phase | 70% | 85% |
| Pellet phase | 24% | 11% |

Example 11 tested at 0.33 g and 0.83 g equated to ~20 mg and ~50 mg active doses. The testing of lower formulation masses in the same medium and same medium volume generates higher bile salt/phospholipid-to-lipid formulation ratios. This is known by those skilled in the art to in some cases to "stress" lipid formulations and trigger increased precipitation of the active. Using rational design approaches for specific actives, however, formulations such as Example 11 can be obtained that show consistent solubilization properties irrespective of the extent of formulation dilution. Indeed, as shown above, Example 11 maintained at least 75% of the active in the solubilized state during digestion under more stressful (i.e., more dilute) conditions. Such consistent solubilization properties are desirable to the development of robust formulations since differences in dilution may be reasonably encountered in vivo through e.g., inter-subject variability in GI fluid volumes or in instances where patients are dosed different number of formulation capsules.

Example 11 In Vitro Performance Comparison to "SMES 1" in WO2014009434A1

WO2014009434A1 discloses several castor oil containing lipid formulations for the active abiraterone acetate. According to WO2014009434A1, SMES 1 consists of 20% wt castor oil, 20% wt Capmul® MCM, 30% wt Span 80 and 30% Kolliphor® EL. This placebo formulation was also prepared here followed by the complete incorporation of the active at a 60 mg/g loading to enable direct in vitro performance comparison to Example 11. Indeed, SMES 1 was subjected to in vitro dispersion and in vitro digestion tests as described above.

On dispersion, SMES 1 formed a milky dispersion indicating the presence of larger oil droplets in comparison to Example 11 which forms a more translucent dispersion. SMES 1 did however protect against precipitation of the active over 6 hours of dispersion.

On digestion of SMES 1, the following results were obtained:

| Digestion time point | Solubilized (lipid + aq. phase) active concentration (μg/mL) "SMES 1" |
|---|---|
| −5 min | 1582 |
| 0 min | 1678 |
| 5 min | 757 |
| 15 min | 614 |

| Digestion time point | Solubilized (lipid + aq. phase) active concentration (μg/mL) "SMES 1" |
|---|---|
| 30 min | 666 |
| 45 min | 774 |
| 60 min | 766 |
| Colloidal distribution of the active @ 60 min: | |
| Lipid phase | 22% |
| Aq. phase | 47% |
| Pellet phase | 31% |

The results show that SMES 1 exhibited a tendency toward precipitation of the active immediately on digestion of the formulation, with over a 50% decrease in solubilized active concentrations between t=0 and t–5 min, As a result, SMES 1 provided substantially lower solubilization after 1 hour digestion in comparison to Example 11 (766 ug/mL vs. 1164 ug/mL). In addition, due to poor dispersibility, the fraction of the active solubilized in the lipid phase was higher for SMES 1 in comparison to Example 11 (22% vs. 10%).

Example 5

The following components were formulated

| Function | Component | Amount (wt %) |
|---|---|---|
| Active | Abiraterone Acetate | 10.0 |
| Low flow point Lipid A | $C_{10}$-$C_{18}$ Triglycerides (Gelucire ® 43/01) | 28.3 |
| Low flow point Surfactant B | Stearoyl macrogol-32 glycerides (Gelucire ® 50/13) | 56.6 |
| High flow point Lipid C | Glyceryl behenate (Compritol ® 888) | 5.0 |
| Antioxidant | Butylated hydroxytoluene (BHT) | 0.1 |

The active-free formulation was prepared first by weighing the appropriate amount of each of the above excipients into a water-jacketed tank, with prior excipient melting at 75° C. Excipients were then mixed thoroughly to generate a single phase solution. The active, (abiraterone acetate) was added and mixed with the molten mixture. Then the molten mixture was allowed to cool to 60° C. The molten mixture was then injected onto a melt-spray congeal apparatus equipped with a spinning disk atomizer spinning at 2050 rpm, maintained at 60° C. and at a s pray rate of 120 g/min. Droplets of the molten mixture were formed and congealed at <5° C. The resulting LMP particles had a generally spherical shape, and a mean particle size of 270 μm.

In Vitro Performance Tests

In vitro digestion tests were performed as follows: 1 g of the active-containing formulation was dispersed in 40 mL fasted intestinal medium (2 mM Tris-maleate, 1.4 mM $CaCl_2 \cdot 2H_2O$, and 150 mM NaCl, 3 mM sodium taurodeoxycholate and 0.75 mM phosphatidylcholine, 37° C.) using a pH-stat titrator as described by the LFCS Consortium (Williams, H D. et al., J. Pharm. Sci. 101 (2012), p. 3360-3380). Digestion was initiated on addition of 4 mL porcine pancreatic extract, prepared as described previously (Williams, H D. et al., J. Pharm. Sci. 101 (2012), p. 3360-3380), and continuously monitored and maintained at pH 6.5 with 0.2 or 0.6 M NaOH for 60 min during which period samples were removed, centrifuged to produce a multiphase sample consisting of; a pellet phase, containing any precipitated and suspended active; an aqueous phase, containing the active in free solution and active solubilized in small micelles and vesicles; and sometimes a lipid phase, containing the active solubilized/suspended in undigested and undispersed solid lipid phases and/or larger colloids such as multi-lamellar vesicles. Active concentration in the aqueous phase was measured by HPLC. The performance of Example 5 on digestion is summarized below. The same test was performed again without adding pancreatic enzyme to evaluate the impact of digestion on drug solubility in the lipidic colloidal species. Also thermodynamic solubility of the active was evaluated in digested placebo formulations for determining solubility in digested lipidic colloidal phases.

| | Example 5 Active concentration (μg/mL) | |
|---|---|---|
| Digestion time | Test 1 | Test 2 (undigested) |
| –5 | 548 | 427 |
| 0 | 623 | 435 |
| 5 | 757 | 519 |
| 15 | 754 | 665 |
| 30 | 593 | 502 |
| 45 | 401 | 640 |
| 60 | 381 | 513 |
| AA solubility in crystalline digestion media | | 27 |
| AA solubility in digested LMP formulations | | 121 |

The results show that the formulation of example 5 was able to sustain the active at concentrations much higher than the equilibrium solubility of the crystalline active in the same medium, which was measured at 27 μg/mL. Example 5 showed evidence of active precipitation on digestion, as evidenced by the decrease in solubilized concentrations once the formulation started to disperse around 15 min. Through Test 2 it is seen that digestion does not greatly impact compound solubilization which is positive. Digestion itself may have promoted "release" of the dissolved/dissolving drug though this might have been masked if released drug rapidly recrystallized. Equilibrium solubility of crystalline active in the digested LMP's was measured at 121 μg/mL, which shows overall improvement in solubilization provided by the digested BS/PL-lipid mixed micellar system; active drug in the aqueous phase containing BS/PL—Lipid-enriched mixed micelles is considered the available form for passing drug through the unstirred water layer to the enterocyte for absorption.

The antioxidant, BHT, was added at a 0.1% wt concentration to Example 5, which were then placed on accelerated chemical stability at 25° C./60% RH and 40° C./75% RH for 1 month. The results are summarized in the table below.

| Example 5 | Active loading (% wt) | 25° C./60% RH | 40° C./75% RH |
|---|---|---|---|
| (1 month) | 10 | <LOQ | <LOQ |

LMP Examples 12 and 13 were also successfully prepared in the same fashion as described above for Example 5:

| Component | Amount (wt %) | |
|---|---|---|
| | Example 12 | Example 13 |
| Abiraterone acetate | 4.00 | 20.00 |
| $C_{10}$-$C_{18}$ Triglycerides (Gelucire ® 43/01) | 30.32 | 24.90 |
| Stearoyl macrogol-32 glycerides (Gelucire ® 50/13) | 60.64 | 49.90 |
| Glyceryl behenate (Compritol ® 888) | 5.00 | 5.00 |
| Butylated hydroxytoluene (BHT) | 0.04 | 0.20 |

Example 12 was subjected to in vitro digestion tests are described for previous formulations. The following results were obtained:

| Digestion time | Example 12 Active concentration (μg/mL) |
|---|---|
| −5 | 811 |
| 0 | 649 |
| 5 | 694 |
| 15 | 658 |
| 30 | 592 |
| 45 | 564 |
| 60 | 811 |

The results show that Example 12 generally provided higher solubilized active concentrations in comparison to Example 5, despite the use of a lower active loading (4% wt vs. 10% wt) and due to the formulation containing a higher fraction or pre-dissolved active in the formulation and the higher formulation:active ratio.

Example 12 was placed on accelerated chemical stability at 25° C./60% RH and 40° C./75% RH for 1 month. The results are summarized in the table below.

| Example 12 (1 month) | Active loading (% wt) | 25° C./60% RH | 40° C./75% RH |
|---|---|---|---|
| | 4 | <LOQ | <LOQ |

In Vivo Performance Assessment of Example 11 in Beagle Dogs Vs. Zytiga® Tablets in Fed/Fasted Study The in vivo absorption of the active was assessed in a further cross-over study in fasted and fed beagle dogs (n=6). In the fed legs of the study, dogs received ~100 g of FDA high-fat diet daily via oral gavage for 3 days before treatment. This meal consisted of 1100-1200 calories, a total mass of 600-700 g and with ~50% of the calories from fat. The meal was homogenized prior to administration. On the day of dosing, dogs received this meal 30 min prior to dosing.

Dogs were randomized over 6 weeks to receive either the commercial abiraterone acetate tablet (Zytiga® 250 mg), Example 11 and Example 5, in a fasted and fed state. The target dose in the lipid formulation (Example 11) and LMP formulation (Example 5) was 50 mg, namely $\frac{1}{5}^{th}$ of the Zytiga® dose. This dose was delivered using approximately 0.83 mL of Example 11, while for Example 5, using approximately 500 mg formulation. Both were filled in hard gelatin capsules (Licaps®, size 00el) prior to administration.

The following results were obtained (results are expressed as measured abiraterone in the plasma due to complete conversion from abiraterone acetate). Results are also presented in FIG. 1.

| Treatment | Dose (mg) | $C_{max}$ ± SD (ng/mL) | $AUC_{0-24\,h}$ (h · ng/mL) | CV | $T_{max}$ (h) | Relative BA |
|---|---|---|---|---|---|---|
| Zytiga ® tablet fasted | 250 | 303.7 ± 313.4 | 713 | 111% | 1.2 ± 0.6 | 100% |
| Zytiga ® tablet fed | 250 | 2401.7 ± 840.0 | 7098 | 39% | 2.1 ± 1.0 | ~1000% |
| Example 11 fasted | 50 | 401.2 ± 99.1 | 852 | 28% | 0.9 ± 0.2 | 119% |
| Example 11 fed | 50 | 373.3 ± 129.8 | 762 | 28% | 1.4 ± 0.5 | 107% |
| Example 5 fasted | 50 | 161.4 ± 71.8 | 351 | 36% | 1.0 ± 0.3 | 49% |
| Example 5 fed | 50 | 185.7 ± 39.1 | 562 | 25% | 2.7 ± 0.5 | 79% |

Consistent with the first dog study performed (described above), the fasted state absorption of the active from the Zytiga® tablet was relatively low and variable. Exposure in the fed state was ~10-fold higher, increasing from 713 h·ng/mL to 7098 h·ng/mL, while the inter-dog variability decreased substantially from 111% in the fasted to state to 39% when co-administered with food. In the same cross-over study, Example 11 achieved a fasted-state exposure of 852 h·ng/mL, which was slightly higher than Zytiga® under the same conditions despite dosing only $\frac{1}{5}^{th}$ of the dose. Example 11 also substantially reduced fasted-state variability in absorption (reduced from 111% to 28%) while absorption from Example 11 was near independent of food—only a small decrease in the extent of absorption in the presence of food (762 h·ng/mL) was observed.

Example 5 did not provide the same level of absorption when compared to Example 11 at a 50 mg dose ($AUC_{0-24\,h}$ values were 351 and 562 h·ng/mL in the fasted and fed state, respectively, compared to 852 and 762 h·ng/mL for Example 11), but Example 5 did achieve a total exposure that was ~50% relative to Zytiga®, while also producing a substantial reduction in variability (36%). In terms of the food-effect, Example 5 exhibited a modest ~1.2-fold increase in exposure in the fed state.

This substantial increase in abiraterone acetate exposure in the presence of food in dogs on dosing Zytiga® tablets is consistent with evidence of a very large food effect (~10-fold) in human subjects. By providing great solubilization of the active in the GI tract, both Example 5 and Example 11 are able to support higher amounts of absorption in the fasted state. This in turn affords the possibility of lower doses, reduced variability and eliminated food-effect as illustrated here by lipid formulation Examples 5 and 11.

See FIG. 1.

Abiraterone plasma concentration versus time data after oral administration of Zytiga® tablet (250 mg abiraterone acetate) or Example 11 capsule (50 mg abiraterone acetate) or Example 5 capsule (50 mg abiraterone acetate) to beagle dogs in either fasted or fed states. Mean±SD.

We claim:
1. A composition, consisting of:
abiraterone acetate; and
a lipid matrix, consisting of (a) a fatty acid ester of glycerol or mixtures thereof in an amount of from 10 wt % to 60 wt % of the composition; (b) a propylene glycol fatty acid ester, or a polyoxylglyceride, or a combination thereof, wherein the propylene glycol fatty acid ester, or the polyoxylglyceride, or the combination thereof is present in an amount of from 20 wt % to 60 wt % of the composition; and (c) a surfactant present in an amount of from 15 wt % to 60 wt % of the composition; and wherein the abiraterone acetate is solubilized in the lipid matrix.

2. A composition, consisting of:
abiraterone acetate;
a lipid matrix, consisting of (a) a fatty acid ester of glycerol or mixtures thereof in an amount of from 10 wt % to 60 wt % of the composition; (b) a propylene glycol fatty acid ester, or a polyoxylglyceride, or a combination thereof, wherein the propylene glycol fatty acid ester, or the polyoxylglyceride, or the combination thereof is present in an amount of from 20 wt % to 60 wt % of the composition; and (c) a surfactant present in an amount of from 15 wt % to 60 wt % of the composition; and wherein the abiraterone acetate is solubilized in the lipid matrix; and
an antioxidant.

3. A capsule filled with the composition of claim 1.
4. A capsule filled with the composition of claim 2.
5. The composition of claim 1, wherein the abiraterone acetate comprises at least 0.2 wt % of the composition.
6. The composition of claim 1, wherein the composition is formulated for being filled into a capsule.
7. The composition of claim 1, wherein the composition is formulated for oral administration to a patient in need of therapy.
8. The composition of claim 1, wherein the fatty acid ester of glycerol is glycerol tricaprylate, glycerol tricaprate, glycerol trilaurate, glyceryl triolein, glyceryl tristearate, glyceryl tripalmitate, almond oil, canola oil, cod liver oil, corn oil, cottonseed oil, evening primrose oil, fish oil, grape seed oil, olive oil, palm kernel oil, palm oil, peanut oil, rapeseed oil, safflower oil, sesame oil, soybean oil, sunflower oil, hydrogenated coconut oil, hydrogenated cottonseed oil, hydrogenated palm oil, hydrogenated soybean oil, partially hydrogenated soybean oil and hydrogenated vegetable oil, glycerol monolinoleate, glycerol monooleate, glycerol monostearate, glycerol monocaprylate, glycerol monocaprate, or mixtures thereof.
9. The composition of claim 1 wherein the polyoxylglyceride is an oleoyl macrogol-6 glyceride, a linoleoyl macrogol-6 glyceride, or a lauroyl macrogol-6 glyceride.
10. The composition of claim 1, wherein the surfactant is Polyoxyl 40 hydrogenated castor oil, a polysorbate, polyoxyl 35 castor oil, polyethoxylated 12-hydroxysteric acid, vitamin E, tocopheryl polyethylene glycol succinate (TPGS), a caprylocaproyl macrogol-8 glyceride, a lauroyl macrogol-32 glyceride, macrogol stearate, or any mixture of these surfactants.
11. The composition of claim 1, wherein
(a) the fatty acid ester of glycerol or mixture thereof is present in an amount of from 20 wt % to 40 wt % of the composition;
(b) the propylene glycol fatty acid ester, or the polyoxylglyceride, or the combination thereof is present in an amount of from 20 wt % to 40 wt % of the composition; and
(c) the surfactant is present in an amount of from 20 wt % to 40 wt %.
12. The composition of claim 1, wherein the fatty acid ester of glycerol is glycerol monolinoleate, glycerol monooleate, glycerol monostearate, glycerol monocaprylate or glycerol monocaprate.
13. The composition of claim 1, wherein the propylene glycol fatty acid ester is propylene glycol monocaprylate, a propylene glycol dicaprate/dicaprylate ester, propylene glycol heptanoate, propylene glycol monolaurate, propylene glycol monostearate, propylene glycol monooleate, propylene glycol monopalmitate, or propylene glycol monomyristate.
14. The composition of claim 1, wherein the fatty acid ester of glycerol is glycerol monooleate and the propylene glycol fatty acid ester is propylene glycol monocaprylate.
15. The composition of claim 1, wherein the abiraterone acetate is present in an amount ranging from 5 wt % to 10 wt % of the composition.

* * * * *